(12) United States Patent
D'Ambrosio et al.

(10) Patent No.: US 8,591,562 B2
(45) Date of Patent: Nov. 26, 2013

(54) METHODS AND DEVICES FOR BRAIN COOLING FOR TREATMENT AND PREVENTION OF ACQUIRED EPILEPSY

(75) Inventors: Raimondo D'Ambrosio, Seattle, WA (US); Matthew Smyth, Frontenac, MO (US); Steven Mark Rothman, Clayton, MO (US); John W. Miller, Bellevue, WA (US); Jason Fender, Bonney Lake, WA (US)

(73) Assignees: University of Washington, Seattle, WA (US); Regents of the University of Minnesota, Saint Paul, MN (US); Washington University in St. Louis, St. Louis, MO (US)

( * ) Notice: Subject to any disclaimer, the term of this patent is extended or adjusted under 35 U.S.C. 154(b) by 558 days.

(21) Appl. No.: 12/629,863

(22) Filed: Dec. 2, 2009

(65) Prior Publication Data
US 2010/0312318 A1     Dec. 9, 2010

Related U.S. Application Data (60) Provisional application No. 61/119,295, filed on Dec. 2, 2008.

(51) Int. Cl.
*A61F 7/12* (2006.01)
(52) U.S. Cl.
USPC .......................................... 607/113; 607/45
(58) Field of Classification Search
USPC ................................................ 607/45, 113
See application file for complete search history.

(56) References Cited

U.S. PATENT DOCUMENTS

| 4,940,052 | A |   | 7/1990  | Mann     |       |
|-----------|---|---|---------|----------|-------|
| 5,311,876 | A |   | 5/1994  | Olsen    |       |
| 5,429,582 | A | * | 7/1995  | Williams | 600/2 |
| 5,611,767 | A | * | 3/1997  | Williams | 600/2 |
| 6,022,308 | A | * | 2/2000  | Williams | 600/2 |
| 6,083,148 | A | * | 7/2000  | Williams | 600/2 |
| 6,146,411 | A |   | 11/2000 | Noda     |       |

(Continued)

FOREIGN PATENT DOCUMENTS

JP     2007-209523     8/2007

OTHER PUBLICATIONS

Rothman, Steven and Symth, Matthew and Yang, Xiao-Feng and Peterson, G.P. "Focal cooling for epilepsy: An alternative therapy that might actually work." Epilepsy and Behavior 7 (2005): 214-221.*

(Continued)

*Primary Examiner* — Linda Dvorak
*Assistant Examiner* — Kaitlyn Smith
(74) *Attorney, Agent, or Firm* — K&L Gates LLP (57) ABSTRACT

A device for cooling the central nervous system (e.g., the brain) is disclosed that is specifically designed to provide cooling of an injured central nervous system for neuroprotective, antiepileptogenic, and/or antiepileptic treatments. In one embodiment, a portion of the cooling device is placed in a recess formed by removal of a portion of a patient's skull. An embedded heat-collecting portion of the cooling device is formed to fit in the location of the formed recess and a thermally conductive material of the heat-collecting portion is placed adjacent the dura mater to provide the desired degree of cooling. A heat-dissipating external plate is in thermal contact with the internal plate, and can be selectively sized according to a specific purpose.

14 Claims, 6 Drawing Sheets

(56) References Cited

U.S. PATENT DOCUMENTS

| | | | |
|---|---|---|---|
| 6,248,126 B1* | 6/2001 | Lesser et al. | 607/113 |
| 6,364,899 B1 | 4/2002 | Dobak, III | |
| 6,506,189 B1 | 1/2003 | Rittman, III | |
| 6,629,990 B2 | 10/2003 | Putz | |
| 6,648,907 B2 | 11/2003 | Larnard | |
| 6,652,566 B2 | 11/2003 | Larnard | |
| 6,793,670 B2* | 9/2004 | Osorio et al. | 607/113 |
| 6,849,072 B2* | 2/2005 | Lee et al. | 606/21 |
| 6,978,183 B2 | 12/2005 | Rothman | |
| 6,986,783 B2 | 1/2006 | Gunn | |
| 7,004,961 B2* | 2/2006 | Wong et al. | 607/105 |
| 7,094,234 B1 | 8/2006 | Lennox | |
| 7,156,867 B2 | 1/2007 | Lennox | |
| 7,204,833 B1* | 4/2007 | Osorio et al. | 606/22 |
| 7,228,171 B2* | 6/2007 | Lesser et al. | 607/3 |
| 7,229,468 B2 | 6/2007 | Wong, Jr. | |
| 7,529,586 B2 | 5/2009 | Wahlstrand | |
| 8,140,152 B2 | 3/2012 | John | |
| 8,202,308 B2* | 6/2012 | Smyth | 607/113 |
| 8,267,983 B2* | 9/2012 | Rogers et al. | 607/104 |
| 2004/0049250 A1* | 3/2004 | Lamard et al. | 607/96 |
| 2004/0082984 A1* | 4/2004 | Osorio et al. | 607/105 |
| 2005/0149123 A1* | 7/2005 | Lesser et al. | 607/2 |
| 2005/0222652 A1 | 10/2005 | Mori | |
| 2005/0273144 A1 | 12/2005 | Lennox | |
| 2006/0173522 A1* | 8/2006 | Osorio | 607/116 |
| 2007/0213784 A1* | 9/2007 | Pless | 607/45 |
| 2008/0140149 A1* | 6/2008 | John et al. | 607/45 |
| 2008/0183097 A1* | 7/2008 | Leyde et al. | 600/545 |
| 2008/0264464 A1* | 10/2008 | Lee et al. | 136/201 |
| 2009/0005843 A1 | 1/2009 | Smyth | |
| 2009/0112273 A1* | 4/2009 | Wingeier et al. | 607/3 |
| 2009/0112277 A1* | 4/2009 | Wingeier et al. | 607/45 |
| 2009/0112278 A1* | 4/2009 | Wingeier et al. | 607/45 |
| 2009/0112279 A1* | 4/2009 | Wingeier et al. | 607/45 |
| 2009/0112280 A1* | 4/2009 | Wingeier et al. | 607/45 |
| 2009/0222059 A1* | 9/2009 | Hillis et al. | 607/45 |
| 2010/0198204 A1* | 8/2010 | Rogers | 606/21 |
| 2010/0217341 A1* | 8/2010 | John et al. | 607/2 |
| 2010/0274237 A1* | 10/2010 | Yamakawa et al. | 606/23 |
| 2011/0172554 A1* | 7/2011 | Leyde et al. | 600/544 |
| 2011/0201944 A1* | 8/2011 | Higgins et al. | 600/483 |
| 2011/0213222 A1* | 9/2011 | Leyde et al. | 600/301 |
| 2012/0310313 A1* | 12/2012 | Rogers et al. | 607/113 |

OTHER PUBLICATIONS

Burton, J.M., et al., "Transcortical Cooling Inhibits Hippocampal-Kindled Seizures in the Rat," Epilepsia 46(12):1881-1887, Dec. 2005.

D'Ambrosio, R., et al., "Functional Definition of Seizure Provides New Insight Into Post-Traumatic Epileptogenesis," Brain 132(10):2805-2821, Oct. 2009.

D'Ambrosio, R., et al., "Post-Traumatic Epilepsy Following Fluid Percussion Injury in the Rat," Brain 127(2):304-314, Feb. 2004.

D'Ambrosio, R., et al., "Progression From Frontal-Parietal to Mesial-Temporal Epilepsy After Fluid Percussion Injury in the Rat," Brain 128(1):174-188, Jan. 2005.

Gasteiger, E.L., et al., "Interictal Afterdischarge in Focal Penicillin Epilepsy: Block by Thalamic Cooling," Experimental Neurology 88(2):349-359, May 1985.

Gluckman, P.D., et al., "Selective Head Cooling With Mild Systemic Hypothermia After Neonatal Encephalopathy: Multicentre Randomised Trial," Lancet 365(9460):663-670, Feb. 2005.

Karkar, K.M., et al., "Comment Letters: Focal Cooling Suppresses Spontaneous Epileptiform Activity Without Changing the Cortical Motor Threshold," Epilepsia 43(8):932-935, Aug. 2002.

Karlov, V.A., "Focal Cooling Suppresses Continued Activity of Epileptic Focus in Patients With Partial Status Epilepticus," Epilepsia 44(12):1605, Dec. 2003.

Sartorius, C.J., and M.S. Berger, "Rapid Termination of Intraoperative Stimulation-Evoked Seizures With Application of Cold Ringer's Lactate to the Cortex: Technical Note," Journal of Neurosurgery 88(2):349-351, Feb. 1998.

Shankaran, S., et al., "Whole-Body Hypothermia for Neonates With Hypoxic-Ischemic Encephalopathy," New England Journal of Medicine 353(15):1574-1584, Oct. 2005.

Testa, G., and P. Gloor, "Generalized Penicillin Epilepsy in the Cat: Effect of Midbrain Cooling," Electroencephalography and Clinical Neurophysiology 36(5):517-524, May 1974.

Yang, X.-F., and S.M. Rothman, "Focal Cooling Rapidly Terminates Experimental Neocortical Seizures," Annals of Neurology 49(6):721-726, Jun. 2001.

Yang, X.-F., et al., "Neocortical Seizure Termination by Focal Cooling: Temperature Dependence and Automated Seizure Detection," Epilepsia 43(3):240-245, Mar. 2002.

* cited by examiner

METHODS AND DEVICES FOR BRAIN COOLING FOR TREATMENT AND PREVENTION OF ACQUIRED EPILEPSY

CROSS-REFERENCE TO RELATED APPLICATION

This application claims the benefit of U.S. Provisional Patent Application No. 61/119,295, filed Dec. 2, 2008, the disclosure of which is hereby expressly incorporated by reference in its entirety.

STATEMENT OF GOVERNMENT LICENSE RIGHTS

This invention was made with Government support under grant numbers NS053928 and NS042936 awarded by National Institutes of Health, and grant number W81XWH-05-2-0072 awarded by U.S. Army Medical Research & Material Command. The Government has certain rights in the invention. The Government has certain rights in the invention.

BACKGROUND

The high incidences of traumatic brain injury (TBI) in both the civilian and military population, and the absence of any prophylactic treatment for acquired epilepsy, such as post-traumatic epilepsy (PTE), create an urgent need to develop broad-spectrum and easily deployable therapeutic strategies. There are currently no ways to prevent the onset of posttraumatic epilepsy (PTE) following head injury. The administration of anticonvulsants after head injury may decrease early post traumatic seizures but has failed to impact the development of long-term epilepsy or improve the incidence of disability or death. Therefore, novel treatment paradigms are needed.

Several in vitro and in vivo studies have demonstrated that brain cooling by 10-20° C. reduces epileptiform activity in seizure models and in humans. Technologies based on cranially-implanted Peltier (thermoelectric) cells powered by batteries are under development to achieve such a high degree of cooling in the brain. However, clinical trials conducted to evaluate hypothermic antiepileptogenesis and neuroprotection have all failed. These clinical trials, which employed whole body cooling by ≥5° C. for a few days post-injury, failed to demonstrate effective treatment and were plagued by side effects, ranging from irregular heartbeat to kidney failure, due to the low body temperature.

The process of epileptogenesis in humans is not known. It is theorized that agents that are neuroprotective may also be antiepileptogenic, but no data is available to demonstrate this. Similarly, the process of ictogenesis (i.e., the precipitation of seizures) is not necessarily the same as epileptogenesis. It is therefore entirely possible that treatments that prevent the precipitation of seizures do not prevent the genesis of epilepsy and, vice versa, those that may prevent the onset of epilepsy may not be capable of shutting down existing seizures.

There are known devices that use active cooling to shut down epileptic seizures (antiepileptic effect). Known devices are based on the assumption that cooling a targeted area of the brain by about 10° C. is necessary to shut down the epileptic focus. Once such device is based on active Peltier cells that cool the brain, including heat pipes to cool deep into the brain. A second exemplary known device uses circulating coolant in tubing implanted within the dorsal hippocampus of a brain to achieve cooling of at least 7° C. in the hippocampus. Unfortunately, such devices are typically highly intrusive (if inserted deep into the brain) and require complex structures (e.g., heat pipes), electronics (Peltier elements), and long-lasting powering elements (e.g., batteries) to produce the necessary cooling. None of the known methods and devices provide continuous prevention of epilepsy (epileptogenesis), but only provide remedial action when a seizure begins so as to lessen the severity of the seizure.

What is desired, therefore, is an improved device for preventing and/or treating acquired epilepsy.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, a method for focally cooling a brain to mitigate or prevent acquired epilepsy is provided, the method comprising implanting a cooling device externally adjacent a portion of a dura mater of a patient having acquired epilepsy, wherein a portion of the cooling device extends out from the patient, such that a portion of the brain of the patient is cooled by the cooling device by not more than 4° C.

In another aspect, a brain-cooling device for focally cooling a brain is provided, the device being sized and configured to extend from an external surface of a dura mater of the brain to project beyond a scalp, the device comprising:

(a) a thermally-conductive cooling insert sized and configured to fit adjacent a portion of the dura mater; and (b) a heat-dissipating plate in thermal communication with the cooling insert, sized and configured to extend beyond the scalp and dissipate heat collected by the cooling insert.

In another aspect, a method for treating a patient suffering from a central nervous system injury is provided, comprising focally cooling a portion of the patient's central nervous system to prevent secondary acquired dysfunction, wherein the cooling is accomplished by implanting a cooling device externally adjacent the dura mater overlying the portion of the central nervous system, wherein the portion of the central nervous system of the patient is cooled by the cooling device by not more than 10° C., and further wherein the cooling device is implanted prior to demonstration of central nervous system in the patient.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Previous studies have suggested that cooling of the brain can assist in providing remedial effects to victims of acquired epilepsy. The specific acquired epilepsy referred to herein is posttraumatic epilepsy (PTE), but it will be appreciated that the provided embodiments are also effective in treating other types of acquired epilepsy (e.g., resulting from stroke). Prior art techniques have focused on a large degree of cooling (e.g., greater than 8° C.) and typically involve embedding a cooling devices deep within the brain (e.g., in the medial temporal lobe). In addition to disadvantages associated with embedding a cooling device directly in the brain, significant cooling of a patient's brain can disadvantageously involve reducing the patient's core body temperature, which may cause other physiological complications. Additionally, known methods focus on reducing the severity of a seizure after it has begun as opposed to preventing epileptogenesis using prophylactic measures, as provided herein.

The present inventors have developed a novel in vivo model of PTE in rats wherein chronic recurrent spontaneous partial seizures appear after a single event of a clinically-relevant model of concussive closed head injury referred to as a fluid percussion injury (FPI). This model represents a significant departure from previous models of acquired epilepsy because the initiating insult, a transient compression of the dura mater without penetration, is mechanically very similar to human cases of concussive closed head injury. In a recently completed blind, randomized preclinical study we made the remarkable observation that FPI-induced seizures can often be prevented by a mild temperature decrease of the injured cortex on the order of just ~1.2° C. These studies indicate that very mild focal cooling of portions of the neocortex, for a significant period of time can reduce the risk of PTE in patients suffering from head injuries. Unlike the relatively large degree of cooling suggested by the prior art, the mild cooling disclosed herein may be achieved using a passive cooling system.

The present invention has been found to produce a significant reduction in the development of PTE with localized focal cooling of the neocortex (brain) through the dura mater using cooling ($\Delta T$) of less than 4° C. and even less than 2° C. The mild cooling indicated by the present invention can be accomplished with an extra-dural focal cooling device, i.e., without penetration of the dura mater.

While cooling is described herein in relation to the dura mater, it will be appreciated that injuries to the central nervous system may rupture the dura, and such a rupture site would be a potential area for use of the provided methods and devices. Thus, if the dura mater is compromised, the provided embodiments can be used directly on the sub-dural central nervous system (e.g., neocortex of the brain).

Cooling is determined by the measurement of a temperature at the interface of the brain and the provided cooling device as compared to the rectal temperature of the same patient.

Disclosed herein is a novel cooling device, specifically designed to perform cooling of an injured central nervous system, for neuroprotective, antiepileptogenic, and antiepileptic treatments. In the current embodiment, a portion of the cooling device is placed in a recess formed by removal of a portion of a patient's skull. The embedded portion of the cooling device may be formed, for example, to fit in the location of a decompressive craniectomy and to achieve the desired degree of cooling. A heat-collecting internal plate is placed in contact with the patient's dura mater. Optional flexible heat-conducting materials may be used to increase the heat transfer to the internal plate. A heat-dissipating external plate is in thermal contact with the internal plate, and can be selectively sized according to a specific purpose. In one embodiment, the external plate can be removed by the caregiver, for example to permit cleaning and changing the wound dressing.

After the desired cooling treatment, the cooling device may be removed and replaced by bone or plates, as per accepted current procedures. In some situations it may be preferable to leave the inner plate implanted for periodic treatment.

The present invention provides methods for brain cooling to prevent epileptogenesis after brain injuries, methods for passive brain cooling to prevent ictogenesis and/or epileptogenesis, and devices for passive brain cooling.

The methods and apparatus disclosed herein have several embodiments, of which many employ a brain-cooling device, as noted above. A brain-cooling device in accordance with the teachings of the present invention will now be described further with reference to the FIGURES.

Figure 1:
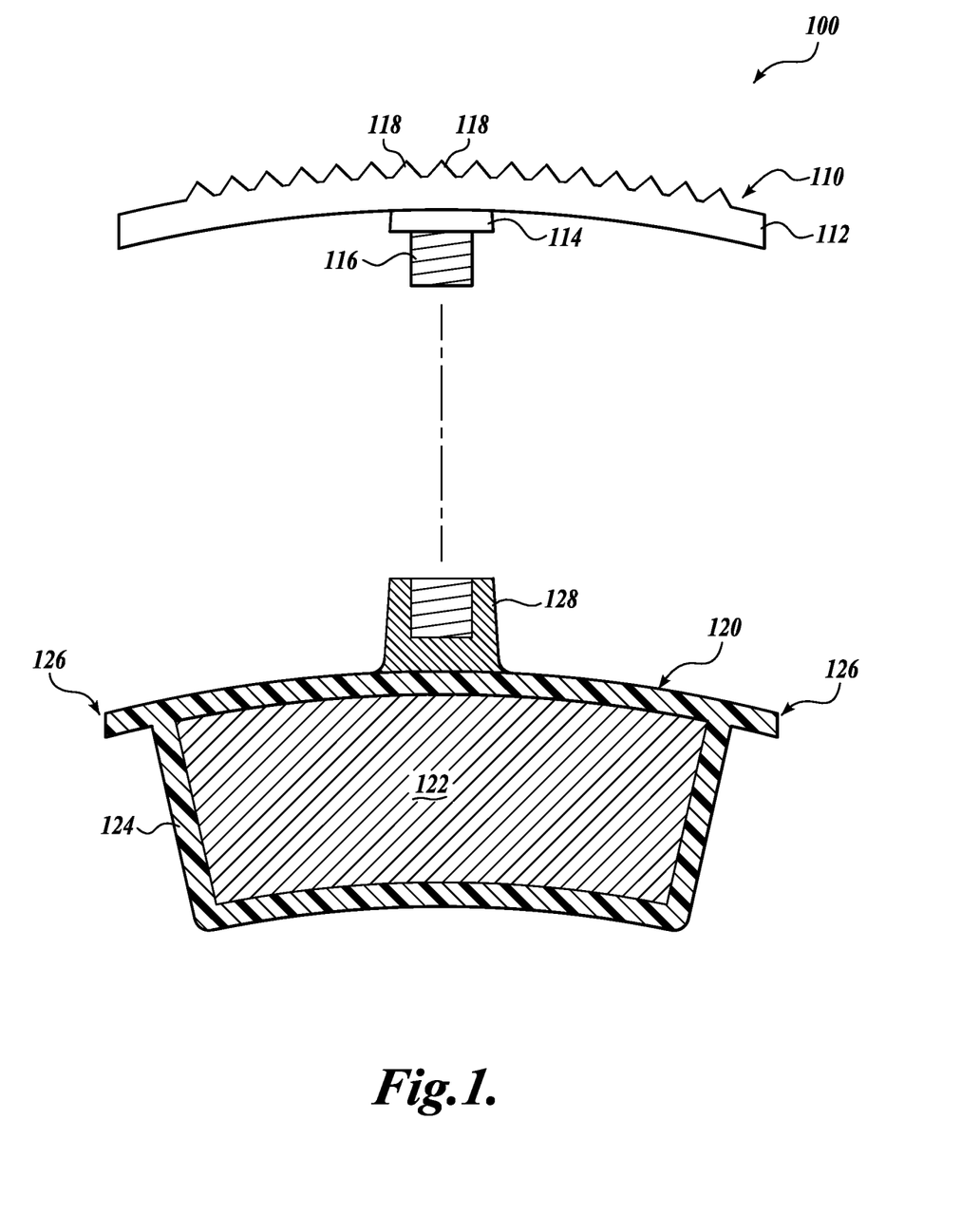
FIG. 1 is a partial cross-sectional view of a representative brain-cooling device as disclosed in the embodiments herein.

FIG. 1 shows a focal brain-cooling device 100 in accordance with the present invention, comprising a heat-dissipating plate 110 and a cooling insert 120. It will be appreciated that the brain-cooling device 100 need not be in two parts, but a separable device, such as that described herein, has advantages for the convenience of the patient when tending to the wound site created by the installation of the device 100.

The heat-dissipating plate 110 in this embodiment includes a base 112 having a shaft 114 on one side including a threaded portion 116. A plurality of fins or ridges 118 are disposed on the opposite side of the base 112 to facilitate heat dissipation. The optional ridges 118 may be formed in other shapes known to those of skill in the art, and can be formed on both the top and bottom of the base 112.

The cooling insert 120 is sized and configured to be inserted into a recess formed by removal of a portion of the patient's cranium, such that the cooling insert 120 contacts the dura mater 95 (see FIG. 3), preferably without compressing the dura mater 95. Direct contact with the brain (e.g., neocortex) is also contemplated; particularly if an injury has ruptured the dura mater 95.

The cooling insert 120 includes a core 122 comprised of a highly thermally conductive material, and an outer portion 124 comprising a thermally conductive biocompatible material. Representative core 122 materials include aluminum, copper, stainless steel, and other materials having high thermal mass and/or high thermal conductivity. The outer portion 124 may be a metal, such as titanium, stainless steel, or any other biocompatible material known to those of skill in the art (e.g., biocompatible polymers). It will be appreciated that the cooling insert 120 may conveniently be formed unitarily, for example of stainless steel or titanium, although such an embodiment is not illustrated herein. A unitary construction requires both high thermal mass/conductivity and biocompatibility. The outer portion 124, and in particular the bottom ("inner") surface of the outer portion 124, is preferably in contact with the dura mater 95 during use of the device 100 to thermally conduct heat away from the patient's neocortex.

The heat-dissipating plate 110 may be made of the same, or different, material as the cooling insert 120 (or core 122), so long as it facilitates passive heat transfer away from the brain. Subcutaneous dissipating strips (see FIG. 9) can be used in conjunction with, or instead of, the externally disposed heat-dissipating plate 110.

A pair of protective wings 126 extend laterally from an upper portion of the cooling insert 120 and position the cooling insert 120 at the desired location on the patient, additionally preventing the cooling insert 120 from compressing the dura mater 95.

A cooling-insert socket 128 is adapted to receive the threaded portion 116 of the heat dissipating plate shaft 114. It will be appreciated that other means for connecting the heat-dissipating plate 110 to the cooling insert 120 are possible and contemplated by the present invention.

Figure 2:
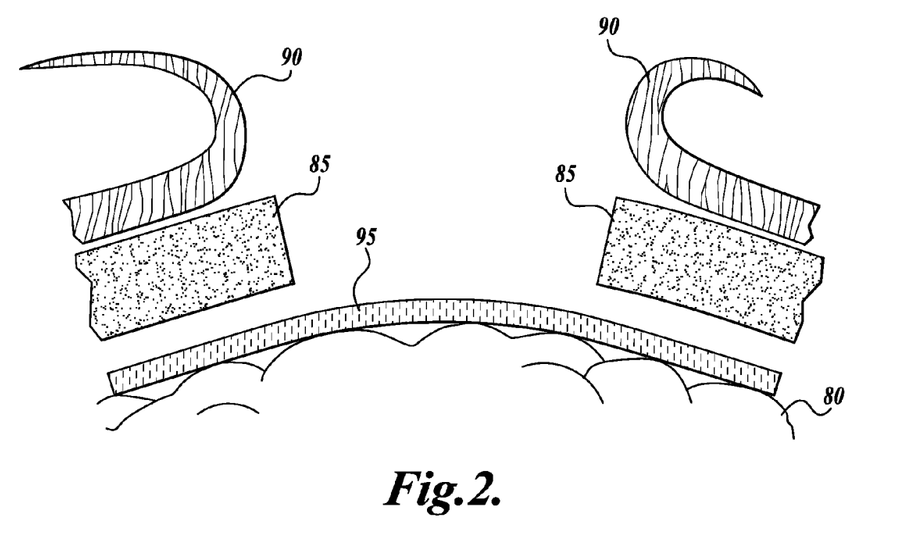
FIG. 2 is a cross-sectional view of a typical craniectomy site wherein bone and scalp are removed to reveal the dura mater surrounding a brain.

FIG. 2 illustrates schematically a craniectomy site wherein a portion of the cranium 85 has been removed through an incision in the scalp 90. The dura mater 95 is revealed above the neocortex 80.

Figure 3:
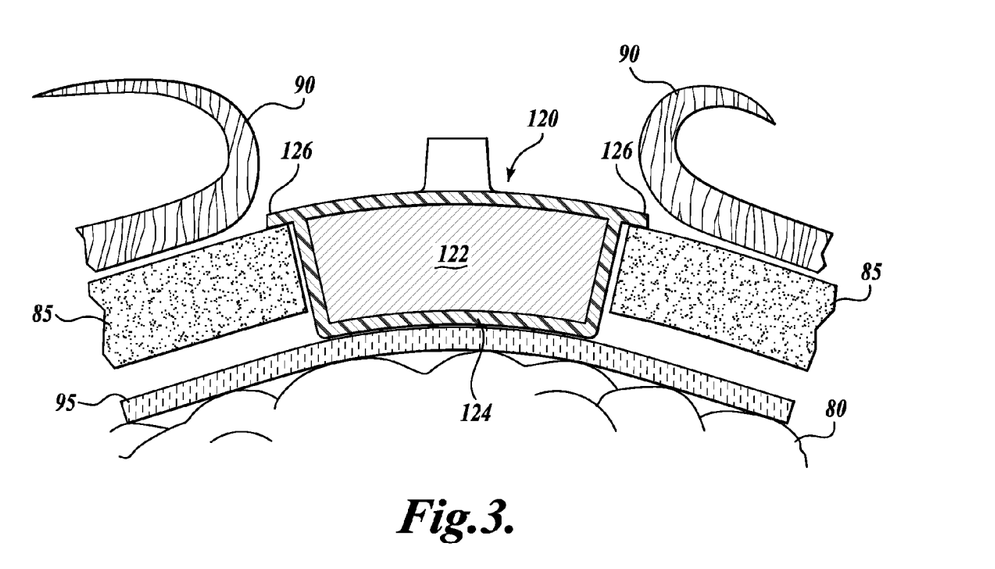
FIG. 3 is a cross-sectional view of a portion of a brain-cooling device shown in FIG. 1 inserted into a craniectomy site.

Referring to FIG. 3, the cooling insert 120 is inserted into the craniectomy site such that the outer portion 124 is adjacent the dura mater 95, providing thermal communication between the neocortex 80 and the cooling insert 120 through the dura mater 95. The protective wings 126 rest on the cranium 85 to prevent pressure being exerted on the dura mater 95 from the cooling insert 120.

Figure 4:
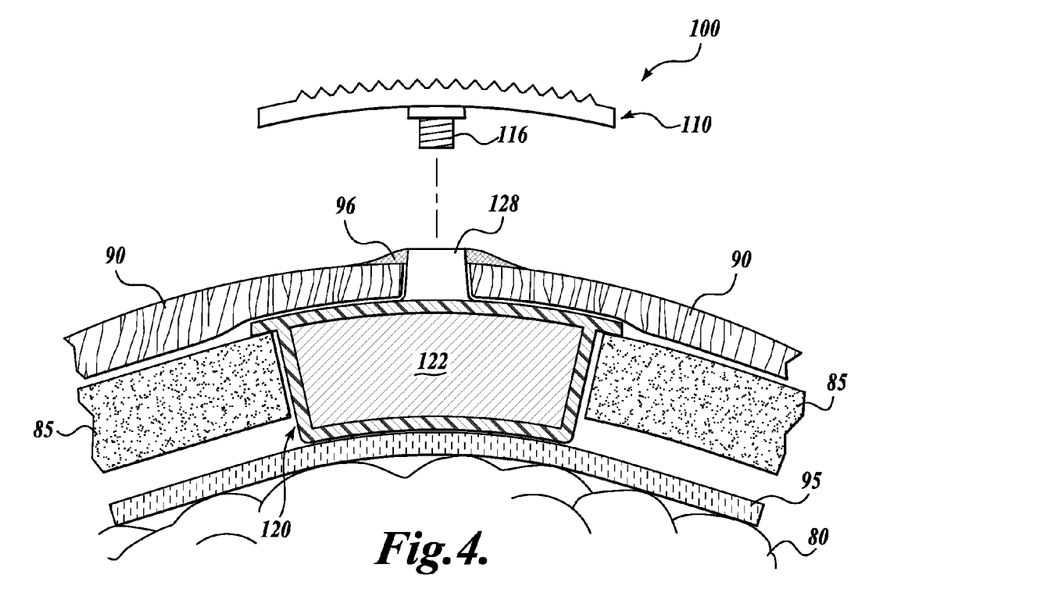
FIG. 4 is a cross-sectional view of a brain-cooling device shown in FIG. 1 embedded within the cranium.

Referring to FIG. 4, the scalp 90 incision is closed over the cooling insert 120 and a wound dressing 96 is applied to the site where the cooling insert socket 128 protrudes beyond the scalp 90. The heat-dissipating plate 110 is illustrated in position to be attached to the cooling insert 120.

Figure 5:
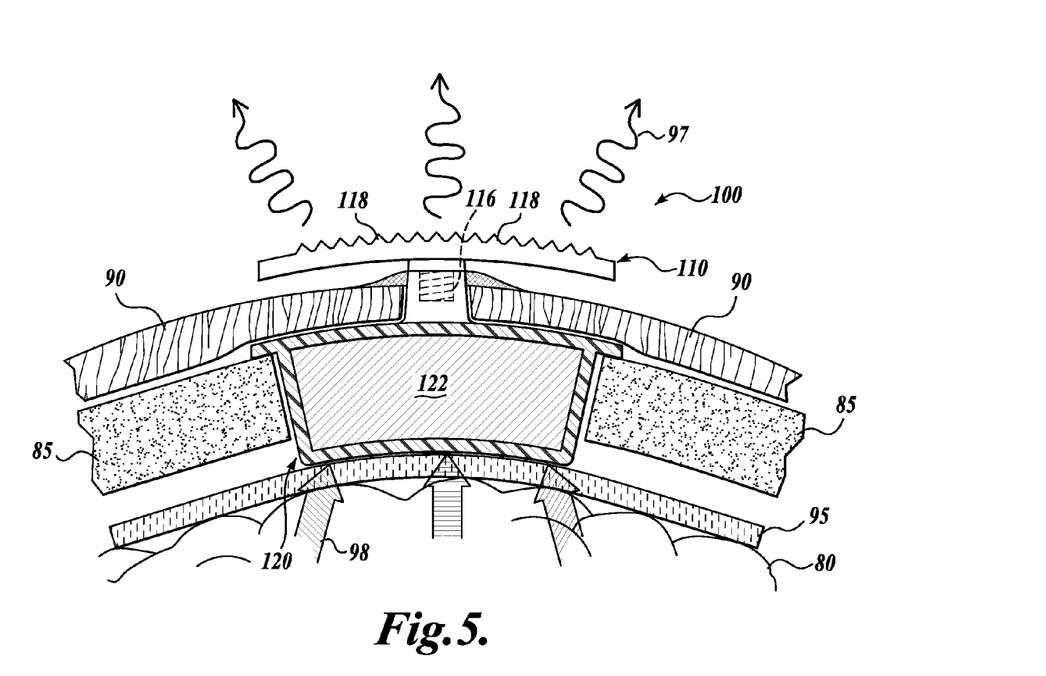
FIG. 5 is a cross-sectional view of the brain-cooling device of FIG. 4, showing the general heat-flow during operation of the brain-cooling device.

Referring to FIG. 5, the brain-cooling device 100 is assembled wherein the cooling insert 120 and the heat-dissipating plate 110 are in thermal, and mechanical, contact. Heat is conducted from the neocortex 80, as illustrated with heat arrows 98 through the dura mater 95 to the cooling insert 120 and thence to the heat-dissipating plate 110, wherein the heat is convectively dissipated to the ambient air, as illustrated with heat arrows 97.

Figure 6:
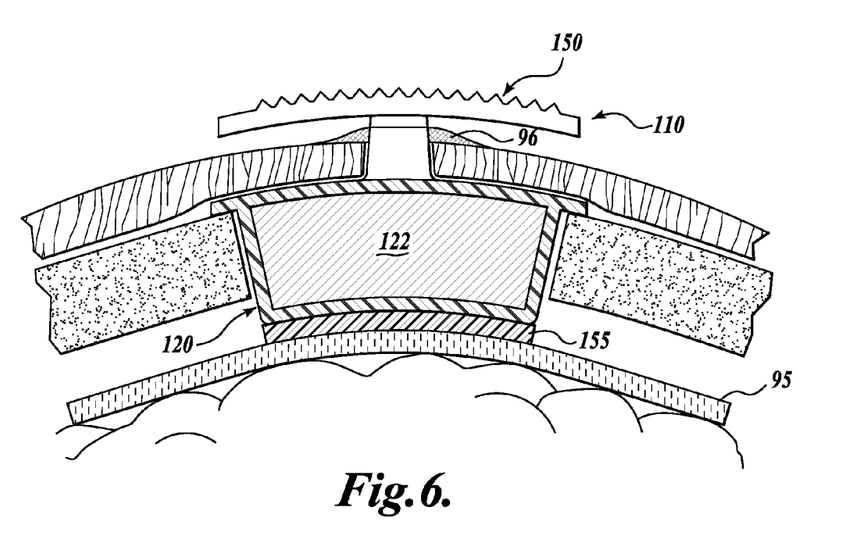
FIG. 6 is a second embodiment of a brain-cooling device in accordance with the present invention, having a conformal polymer layer adjacent the dura.

A second embodiment of a brain-cooling device 150 is shown in FIG. 6, implanted in a patient. The brain-cooling device 150 is similar to the above-described device 100. In this embodiment, a thermally conductive conformable element such as a polymer layer 155 is provided on the cooling insert 120, sized and configured to provide conformal contact with the dura mater 95. For example, the polymer layer 155 may be formed from a "soft" polymer such as a silicone (e.g., a polysiloxane). The soft nature of the polymer layer 155 allows for a more conformal contact with the dura mater 95, to improve heat transport to the cooling insert 120.

Figure 7:
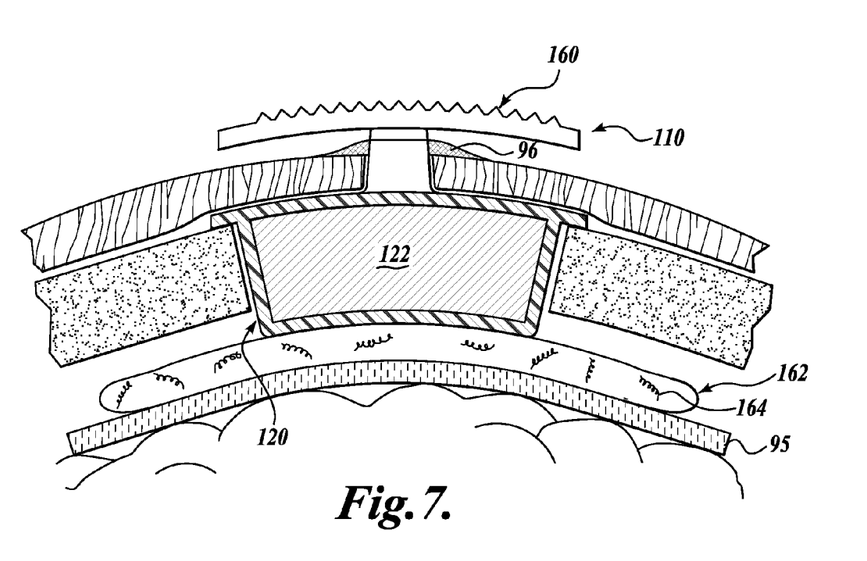
FIG. 7 is a third embodiment of a brain-cooling device in accordance with the present invention, having a thermally conductive biocompatible cushion adjacent the dura.

Another embodiment of a brain-cooling device 160 is shown in FIG. 7. The brain-cooling device 160 is similar to the device 100 described above, and includes a heat-collecting element comprising a thermally-conductive biocompatible cushion 162. In this exemplary embodiment the cushion 162 includes a silicone sack filled with a fluid (e.g., a saline fluid) and optional thermally conductive filaments 164 (e.g., steel wool). The cushion 162 provides a larger area of contact with the dura mater 95 and readily conforms to the dura mater 95. The composition of the cushion 162 allows for good thermal transport between the dura mater 95 contacted by the cushion 162 and the cooling insert 120.

Figure 8:
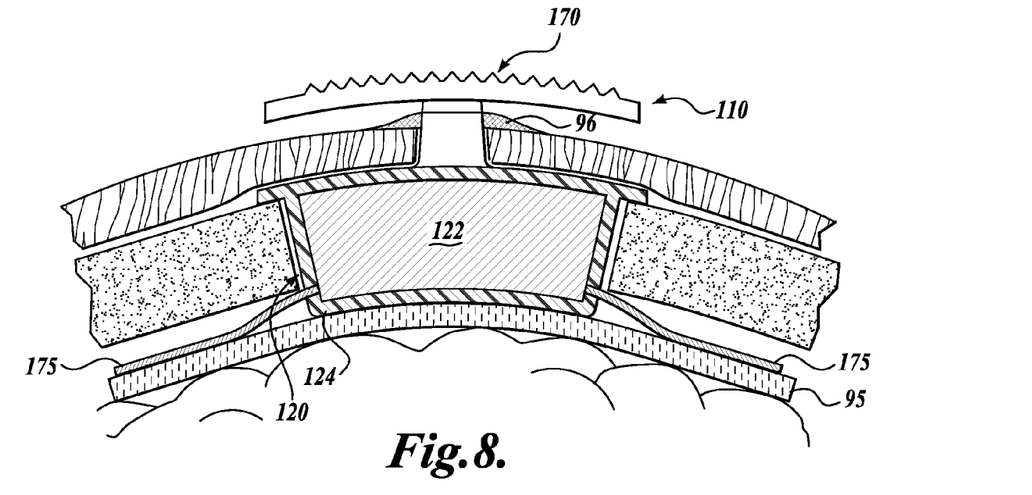
FIG. 8 is a fourth embodiment of a brain-cooling device in accordance with the present invention, having heat-collecting strips in contact with the dura.

Another embodiment of a brain-cooling device 170 in accordance with the present invention is shown in FIG. 8. In this embodiment a heat-collecting element is illustrated comprising cooling strips 175 that are directly linked to the core 122 and provide a mesh, webbing, or stripping extending out from the core 122 to cover a larger area of the dura 90 than that covered by the core 122. The cooling strips 175 can be extra-dural or trans-dural (not illustrated). The cooling strips 175 have good thermal conductivity, and are also biocompatible. In one embodiment, the cooling strips are similar in composition to the core 122 and outer portion 124 of the cooling insert 120 (e.g., a metallic core surrounded by a biocompatible coating).

While not illustrated, the cooling device internal plate optionally includes a temperature sensor that is operationally connected to an external temperature monitor. In one embodiment, the external temperature monitor is mounted on the brain-cooling device, for example, on the heat-dissipating plate. The temperature sensor optionally includes communication means for transmitting the measured temperature to an off-patient monitoring system (e.g., a computer configured to monitor and log temperature) so as to allow for electronic access, manipulation, and monitoring (e.g., automated notification of doctors if certain temperature thresholds are breached) of the temperature measured by the device.

Figure 9:
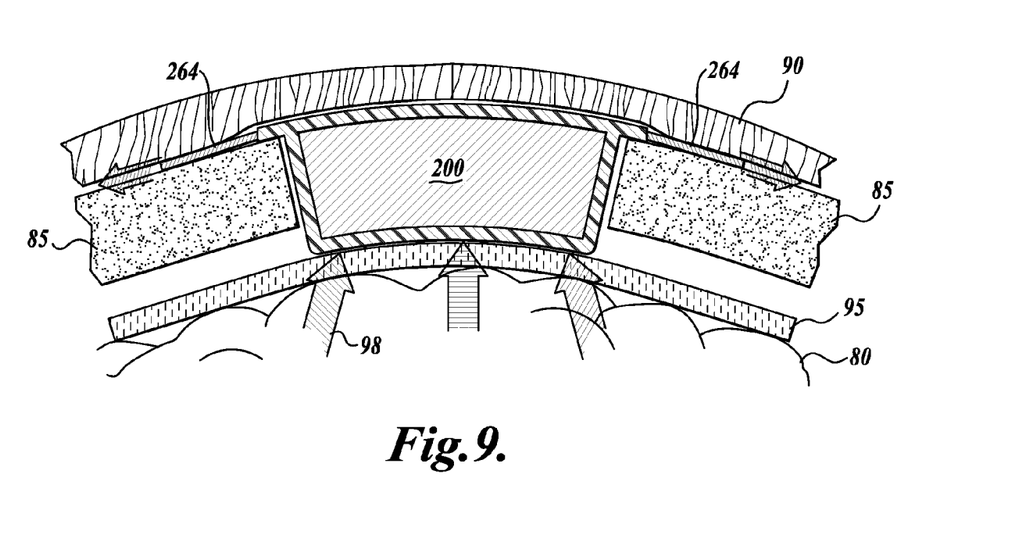
FIG. 9 is a fifth embodiment of a brain-cooling device in accordance with the present invention, comprising a heat-collecting insert without an external heat-dissipating plate.

FIG. 9 illustrates another embodiment of a focal brain-cooling device 200 in accordance with the present invention, wherein no external dissipating plate is used. The scalp 90 can therefore be fully closed over the implanted device 200. The brain-cooling device 200 may be substantially the same as the cooling insert 120 described above, but without the shaft 114 portion, wherein heat dissipation through the scalp 90 provides the desired heat rejection to achieve the mild temperature reduction, e.g., 1°-4° C., as contemplated herein.

Optionally, high thermal conductivity subdermal cooling strips 264 may be provided, that are in thermal communication with the brain-cooling device 200, and extend laterally between the patient's scalp 90 and cranium 85. Additional elements, such as the polymer layer 155, cushion 162, or cooling strips 175, as described above, may also be used with the cooling device 200.

The cooling device shown in FIG. 9 may alternatively comprise an active cooling element (not illustrated), such as a thermoelectric cooler, as is known in the art, to achieve desired levels of cooling in the brain. The active cooling device may be advantageous, for example, to achieve higher cooling levels, for example focal brain cooling of up to 10° C.

The present invention provides methods and devices for treating and/or preventing epilepsy. The inventors of the present invention discovered that focal cooling is both anti-epileptic and antiepileptogenic. With the employment of seizures induced by a realistic injury, and in the absence of pro-convulsant drugs, it is found that cooling by as little as 1.2° C. is sufficient to prevent and block seizures. The finding is notable because it is the first demonstration that minimal (e.g., <2° C.) cooling can prevent or slow down epileptogenesis; and a disease-modifying effect was observed by passive focal cooling at room temperature.

This invention further encompasses novel prosthetic devices specifically designed to perform passive cooling of an injured central nervous system for neuroprotective, antiepileptogenic, and antiepileptic treatments. Passive brain cooling is not considered in known devices and methods because it has been assumed that therapeutic effects would only be achieved by significant cooling. The below-presented experimental data show otherwise.

The provided device can be removed and replaced by bone or plates, as per accepted current procedures, or left implanted chronically for continuous treatment.

In one aspect, a method for treating a patient suffering from a central nervous system injury is provided. In this aspect, the patient has not experienced epileptogenesis, and the method is performed as a prophylactic measure so as to prevent (and/or mitigate) acquired epilepsy and epileptogenesis.

In one embodiment, the method comprises focally cooling a portion of the patient's central nervous system to prevent secondary acquired dysfunction, wherein the cooling is accomplished by implanting a cooling device externally adjacent the dura mater overlying the portion of the central nervous system, wherein the portion of the central nervous system of the patient is cooled by the cooling device by not more than 10° C., and further wherein the cooling device is implanted prior to demonstration of central nervous system in the patient.

Any of the previously described devices (e.g., FIGS. 1-9) are compatible with the method. While passive cooling devices have been emphasized above, active cooling devices (e.g., thermoelectric coolers) are useful in this embodiment (i.e., FIG. 9) wherein an exclusively sub-dermal cooling implant can be used to focally cool the traumatized area of the brain to prevent epileptogenesis while saving the patient from the likely discomfort of having an externally-mounted heat-dissipating element 110.

A typical course of events related to performing the method include: the occurrence of a traumatic injury to the central nervous system (e.g., a FPI to the brain); a craniectomy at the site of the FPI to install a cooling device as provided herein; and focal cooling using the cooling device. As described herein, mild focal cooling has a preventative and mitigating effect on acquired epilepsy. If a cooling device can be installed and focal cooling initiated prior to epileptogenesis, acquired epilepsy can be prevented, or the symptoms greatly mitigated.

The following description of experimental results achieved using exemplary embodiments of the provided methods and devices will now be described. These exemplary results are provided for the purposes of illuminating, and not limiting, the invention.

In a series of experiments, the most practical way to cool the surface of a rat neocortex was determined. Using ambient temperature (~21° C.) as a reference heat sink, a range of rat headsets (i.e., brain-cooling devices 100, 150 of the invention) that dissipated heat from a constant source of heat (electric heating filament) to the room were tested.

The headsets included heat-dissipating metal rods of 4 mm in diameter and of different lengths (thus different thermal mass) to achieve varying dissipating capacities, which were measured directly in preliminary experiments. Four different headsets (A-D) were designed with progressively higher heat-dissipating capabilities in order to test a dose-response effect of cooling on FPI-induced epileptogenesis. To assemble the headset on the animals, the rod was gently placed in contact with the dura mater without compressing it, and five epidural electrodes were implanted for standard ECoG recordings. The electrodes and the metal rod were then enclosed within dental cement, creating a durable headset. The only difference between the 4 types of headset was the thickness of the metal piece (i.e. heat-dissipating plate 110). Headset A was a control and included a 250-μm-thick stainless steel disk of 4 mm in diameter, placed directly adjacent the injured dura. Headset B had a stainless-steel disk of 4 mm in diameter and 1.5 mm in height, that provided the exact same surface contact with the dura as headset A, but had improved cooling due to the larger thermal mass and volume of the stainless-steel piece. Headset C was similar to B, but the metal piece consisted of a stainless-steel rod 4 mm in diameter and 15 mm in height, which extruded from the dental cement chasing. Headset D was similar to headset C, but the bottom of the metal rod was painted with a thin layer of silicone (e.g., polymer layer 155) to prevent direct interface between dura and metal. Headset D was designed to provide maximum contact (thus maximum cooling) between the brain and the thermal mass through the silicone, and also provide a control for the surface contact between dura mater and stainless steel.

In a study in vivo that included ten FPI animals receiving either headset A or C and a temperature probe, it was found that headset C (n=5 animals) induces neocortical cooling by 1.2° C. compared to control headset A (n=5 animals), without affecting body temperature. There was no induction of systemic side effects to the treatment. This mild degree of cooling was applied focally directly to the injured cortex.

A blind and randomized study of the effect of mild cooling on FPI-induced epileptogenesis was conducted as follows. Animals first received FPI as per a standardized procedure. Six days later they were randomized to one of the four types of cooling headsets. The group size was set to nine.

Cooling began immediately upon installation of the headsets. Video-ECoG recordings (continuous 24 hours) of the animals were then acquired after 8, 15, 22, and 29 days of cooling, at 2, 3, 4, and 5 weeks post-injury, respectively. At the end of the chronic cooling period, the steel rods of headsets C and D were re-warmed to 37° C. by passing current through an insulated resistor wrapped around the metal rod protruding out of the acrylic chasing. Rewarming lasted 6-8 hours in each animal during which video-ECoG was acquired. Animals were then processed for pathology, and densitometric analysis of the GFAP+ immunostaining was performed. All data analysis (ECoG and densitometry) was performed blind to the headset.

The results of the above experiments indicate a robust antiepileptogenic effect of focal cooling at modest temperature decreases (less than 2° C.). Varying magnitudes of focal cooling were applies six days after FPI, and the effect on antiepileptogenesis was recorded. While 100% of animals without focal cooling (headset A) went on to develop neocortical chronic recurrent spontaneous partial seizures (CR-SPSs), only half of the animals focally cooled for three weeks at the injury site developed CRSPSs.

Figure 10:
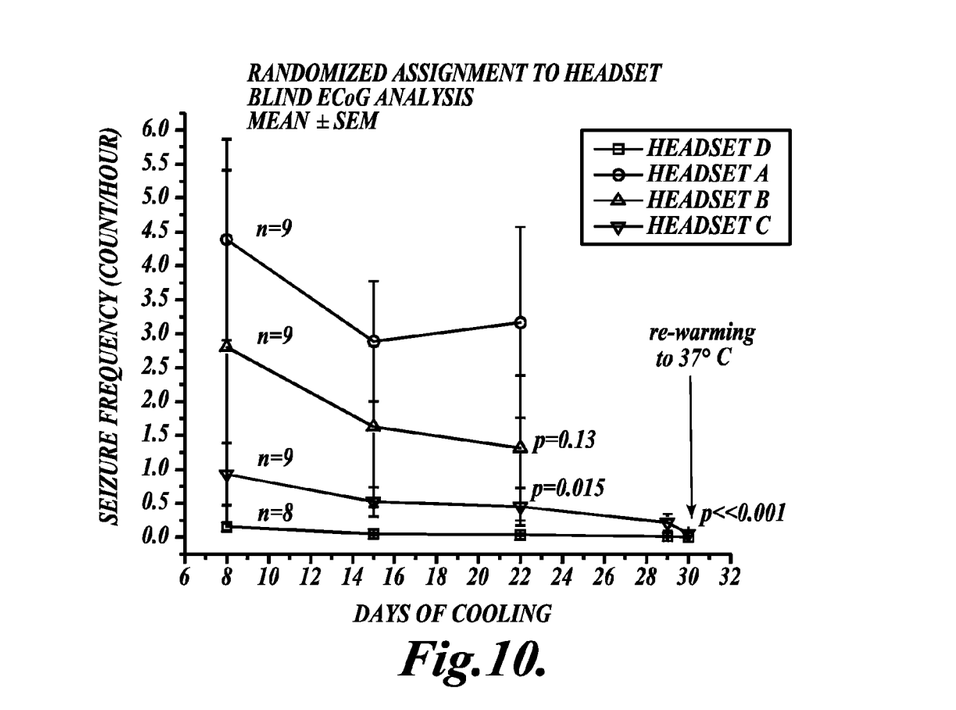
FIG. 10 is a graph illustrating the experimental impact of the use of mild brain cooling methods as disclosed herein on laboratory animals for reducing acquired epileptic seizures, comparing the frequency of seizures for various heat-dissipating headsets.

Blind analysis of the ECoG data during the three-week course of cooling confirmed a dose-dependent decrease in seizure frequency, as illustrated in FIG. 10. FPI rats with headset D had almost a complete absence of ictal events, while those with headset A had robust epilepsy with frequent seizures. Headsets B and C, with intermediate degrees of cooling, had intermediate levels of seizure frequency during the cooling periods. Notably CRSPSs were almost completely prevented by headset D, a result unattainable through the effect of medications such as valproate and carbamazemine.

Animals with headsets C and D, which had the metal rod protruding out of the acrylic chasing, were studied for an additional week to test whether re-warming restored epilepsy. It was determined that seizure activity was not reinstated or increased after rewarming the neocortex for 6-8 hours. Thus, focal cooling prevented PTE in these experiments.

Figure 11:
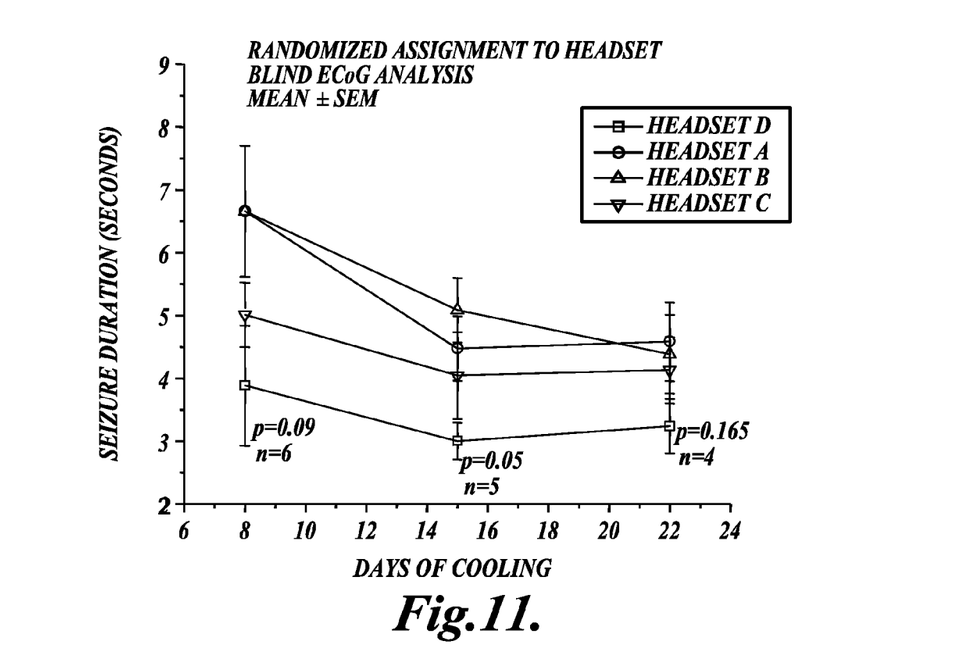
FIG. 11 is a graph illustrating the reduction in duration of acquired epileptic seizures using the embodiments disclosed herein, comparing the duration of seizures for various heat-dissipating headsets.

Next, the duration of neocortical seizures (G1 and G2) in epileptic animals was blindly analyzed, and a similar dose-dependent effect on seizure duration was determined, with the most-cooled animals (headsets C, D) displaying significantly shorter seizure duration than the control animals with headset A, as illustrated in FIG. 11. A blind densitometric analysis of GFAP immunoreactivity revealed no increase in astrogliosis (one of the most sensitive markers of pathology (in cooled versus. control animals), indicating no pathological response to the prolonged mild focal cooling of the neocortex.

In summary, it was determined that a prolonged 1°-2° C. focal cooling of the injured neocortex over three weeks post-injury by a passive device is antiepileptogenic, prevents the onset of FPI-induced epilepsy that is resistant to valproate and carbamazepine, and yet is well tolerated by animals, as it does not affect core body temperature and does not induce pathology. Notably, cooling was initiated six days after head injury, and still demonstrated a potent antiepileptogenic effect.

The invention is not limited to use with PTE sufferers, but can also be extended to other central nervous system injuries that would benefit from local mild cooling of the brain (e.g., stroke victims), as well as those suffering from pharmacoresistant neocortical epilepsy, and lead to the rapid development of prophylactic strategies based on prolonged minimal cooling of the injured brain or epileptic focus, without the side effects observed in previous clinical trials involving lowering core temperature after head injury or the technological challenges of safely achieving the at least 8°-10° C. cooling previously assumed necessary for prevention of epilepsy.

While illustrative embodiments have been illustrated and described, it will be appreciated that various changes can be made therein without departing from the spirit and scope of the invention.

The embodiments of the invention in which an exclusive property of privilege is claimed are defined as follows:

1. A method for mitigating or preventing epilepsy by focally cooling a brain, the method comprising:
    removing a portion of a cranium through an incision in a scalp of a patient to form a recess in which a portion of dura mater is exposed; and
    implanting a cooling device adjacent the exposed portion of dura mater and closing the incision such that an adjacent portion of the brain is cooled by the cooling device by heat dissipation through the scalp, and wherein the adjacent portion of the brain is cooled by not more than 4° C.,
    wherein the cooling device comprises a passive cooling device having a highly thermally conductive portion adjacent the exposed portion of dura mater.

2. The method of claim 1, wherein the portion of the brain is cooled by the cooling device by about 2° C.

3. The method of claim 1, wherein the cooling device does not cause a core body temperature of the patient to decrease.

4. The method of claim 1, wherein the cooling device does not penetrate the dura mater.

5. The method of claim 1, wherein the highly thermally conductive portion comprises a core and an outer portion encasing the core.

6. The method of claim 5, wherein the core is a non-biocompatible material and the outer portion is a biocompatible material.

7. The method of claim 1, wherein the highly thermally conductive portion comprises a metal plate having an inner face, and a polymeric layer disposed between the metal plate inner face and the patient dura mater.

8. The method of claim 1, wherein the cooling device cools the portion of the brain for an extended period of time comprising more than two days.

9. The method of claim 1, wherein the cooling device further comprises at least one thermally conductive subdermal cooling strip configured to extend laterally between the scalp and the cranium.

10. The method of claim 1, wherein the cooling device further comprises a thermally conductive cushion on a proximal face that is in contact with the exposed portion of dura mater.

11. The method of claim 10, wherein the thermally conductive cushion comprises a silicone sack filled with a fluid.

12. The method of claim 11, wherein the thermally conductive cushion further comprises thermally conductive filaments disposed with the silicone sack.

13. The method of claim 1, wherein the cooling device further comprises a plurality of thermally conductive cooling strips that directly engage the dura mater.

14. A method for mitigating or preventing epilepsy by focally cooling a brain, the method comprising:
    removing a portion of a cranium through an incision in a scalp of a patient to form a recess in which a portion of dura mater is exposed; and
    implanting a cooling device adjacent the exposed portion of dura mater and closing the incision such that an adjacent portion of the brain is cooled by the cooling device by heat dissipation through the scalp, and wherein the adjacent portion of the brain is cooled by not more than 4° C.,
    wherein the cooling device further comprises a thermally conductive cushion on a proximal face that is in contact with the exposed portion of dura mater, the thermally conductive cushion comprising a silicone sack filled with a fluid and thermally conductive filaments disposed within the silicone sack.

* * * * *